United States Patent [19]

Marshall

[11] Patent Number: 5,896,034
[45] Date of Patent: Apr. 20, 1999

[54] METHOD AND APPARATUS FOR DETECTING AND MONITORING CORROSION

[75] Inventor: Rodney John Marshall, Southampton, United Kingdom

[73] Assignee: Avonwood Developments Limited, Wimborne, United Kingdom

[21] Appl. No.: 08/649,456

[22] Filed: May 17, 1996

[30] Foreign Application Priority Data

Jul. 6, 1995 [GB] United Kingdom .................. 9513800

[51] Int. Cl.$^6$ .................. G01N 17/04; G01N 27/04
[52] U.S. Cl. .................. 324/700; 324/693; 204/404; 205/776.5; 205/777
[58] Field of Search .................. 324/693, 699, 324/700, 722, 724, 71.2; 204/404; 422/53; 205/775.5, 776.5, 777

[56] References Cited

U.S. PATENT DOCUMENTS

| 3,264,561 | 8/1966 | Gustafson | 324/700 |
|---|---|---|---|
| 3,331,021 | 7/1967 | Marsh et al. | 324/700 |
| 4,217,544 | 8/1980 | Schmidt | 324/700 |
| 4,262,247 | 4/1981 | Olson et al. | 324/700 |
| 4,412,174 | 10/1983 | Conlon et al. | 324/700 |
| 4,514,681 | 4/1985 | Finley et al. | 324/700 |
| 4,800,165 | 1/1989 | Oka et al. | 324/700 X |
| 4,806,849 | 2/1989 | Kihira et al. | 324/700 |
| 5,036,287 | 7/1991 | Serwatzky | 324/700 |
| 5,214,387 | 5/1993 | Fenner | 324/557 |
| 5,221,893 | 6/1993 | Kondou et al. | 324/71.2 |
| 5,243,298 | 9/1993 | Runner | 324/700 |
| 5,403,550 | 4/1995 | Wietek | 422/53 |
| 5,423,298 | 9/1993 | Runner | 324/700 |
| 5,448,178 | 9/1995 | Chen et al. | 324/700 |
| 5,481,198 | 1/1996 | Patel | 324/700 |
| 5,712,559 | 1/1998 | Moore et al. | 324/71.1 |

FOREIGN PATENT DOCUMENTS

| 0354096 | 2/1990 | European Pat. Off. . |
|---|---|---|
| 0495259 | 7/1992 | European Pat. Off. . |
| 1021922 | 3/1966 | United Kingdom . |
| 1261424 | 1/1972 | United Kingdom . |

*Primary Examiner*—Glenn W. Brown
*Attorney, Agent, or Firm*—Richard M. Goldberg

[57] ABSTRACT

Corrosion is monitored by making a resistance measurement between a contact and an uncorroded or relatively uncorroded portion of the article to be monitored. Changes in the resistance measured are a result of the presence of a corrosion product, or the breakdown of protective coatings by corrosion. The contact may be a sensor washer which is held in place around a threaded stud 6 by nut 12. The washer comprises a steel ring 14 and an electrically conducting ring 18 which is insulated from ring 14 and contacted by circling 21 and conductor wire 23 in resin jacket 22. The measurement may be made on magnesium alloy gearboxes in helicopter. The alloy may be protected by a paint film so that the initial resistance measured is very high.

24 Claims, 2 Drawing Sheets

METHOD AND APPARATUS FOR DETECTING AND MONITORING CORROSION

This invention relates to the detection and monitoring corrosion in metal articles and is particularly but not exclusively, concerned with monitoring corrosion in magnesium or other alloy articles in a corrosive environment.

A particular example of such a need is in a magnesium alloy gear box used in a helicopter and open to attack by sea water.

Helicopters, particularly those based on board aircraft carriers or other sea-going vessels and those based on shore-line establishments are particularly prone to problems associated with corrosion in their gear box and other magnesium alloy castings due to the presence of saline spray induced by their rotors. Any such corrosion needs to be carefully monitored and suitable action taken when the tolerated level of corrosion is approached or exceeded.

Corrosion such as micro galvanic corrosion and accelerated macro galvanic corrosion is found to occur in any or all parts of the magnesium alloy casting including the vicinity of the bolt fixings where the gear box head is mounted to the gear box mounting flange, and this forms a convenient location for sensing and monitoring corrosion in the adjacent structure.

We have found that despite the fact that corrosion occurs via a conventional electro chemical mechanism, effects due to the presence of an electrolyte, such as sea water, are only spasmodic. After corrosion has taken place there is a tendency for the affected areas to dry out, thereby rating previous proposals for electro chemical measurement such as linear polarization resistance or zero resistance amperometry ineffectual. In addition, under dry conditions previous proposals for electro chemical measurement would fail by indicating "no corrosion" and thus be intrinsically unsafe. Therefore, a need for improvement in the methods and apparatus for detecting and monitoring such corrosion has been identified.

An object of the present invention is to provide improvements in relation to one or more matters discussed herein or generally.

According to the invention there is provided a method and apparatus wherein a resistance measurement is made between a contact and an uncorroded or relatively uncorroded portion of the article to be monitored.

The method is capable of operating on bare magnesium or surfaces protected by coatings such as paints, greases, etc.

The method and apparatus of the embodiments provides means for the detection and monitoring of corrosion which is capable of operating under dry or wet conditions.

The embodiments also provide a method and apparatus for detecting and monitoring corrosion whereby such corrosion is measured as the change in the resistance measurement between a contact and an uncorroded or relatively uncorroded portion of the article to be monitored due to the presence of a corrosion product.

In an embodiment of the invention there is provided a contact resistance sensor which measures the changes in resistance across a contacting pad initially in good contact with an uncorroded portion of the article to be monitored, such as an alloy gear box, such changes in resistance being as a result of the presence of the corrosion product MgO or $Mg(OH)_2$, this being a good electrical insulator.

In an embodiment of the invention there is provided a contact resistance sensor which measures the changes in resistance across a contacting pad with an uncorroded paint protected portion of the article to be monitored such as an alloy gearbox, such changes in resistance being a result of the protective film being broken by the corrosion process, to cause a transition from a very high resistance to a low resistance In a further embodiment of the invention the contact resistance sensor is incorporated into a washer.

In a still further embodiment of the invention measurement of resistance is made by use of ring probes which permit measurement around the circumference of the washer rather than at a single point. Testing showed these to be equally effective provided access to the outside environment was made through slots in the casing.

An embodiment of the invention will now be described by way of example only with reference to the accompanying drawings in which FIG. 1 is a section view of part of a typical magnesium member with a probe according to the invention;

Figure 1:
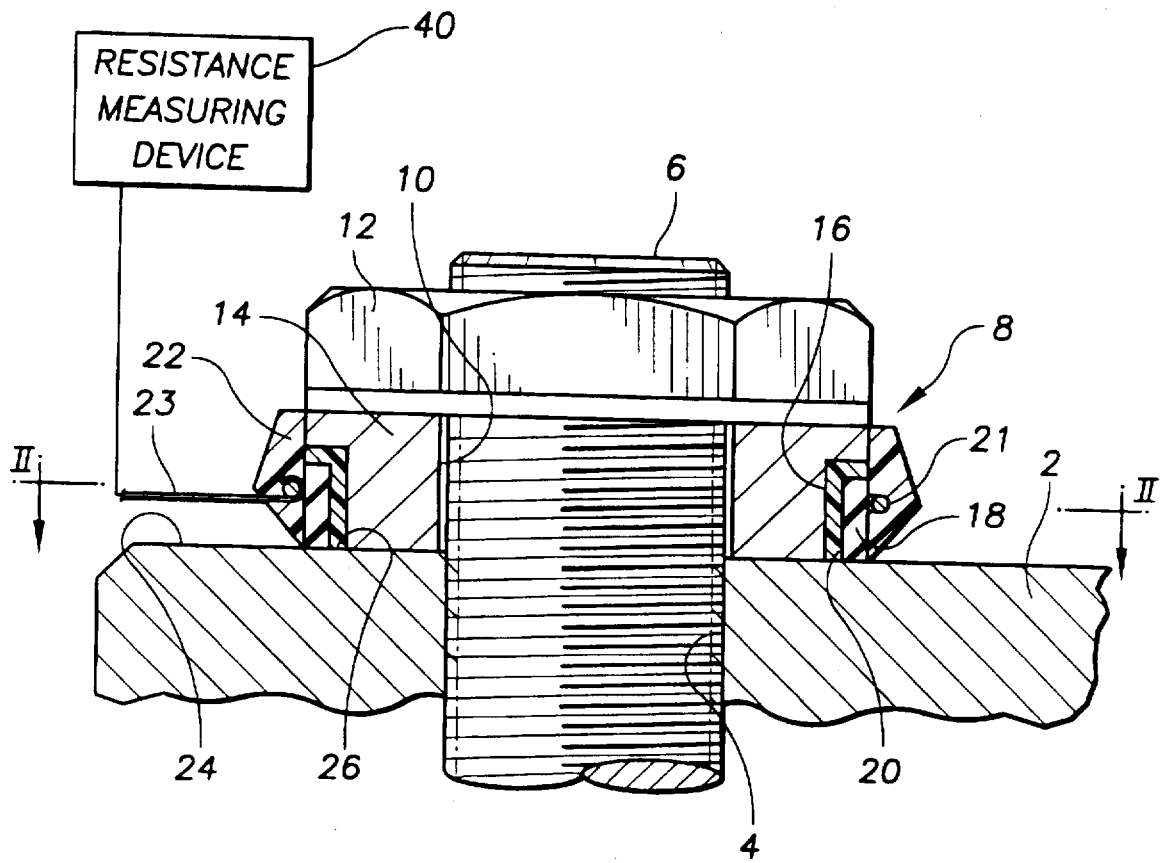
Figure 2:
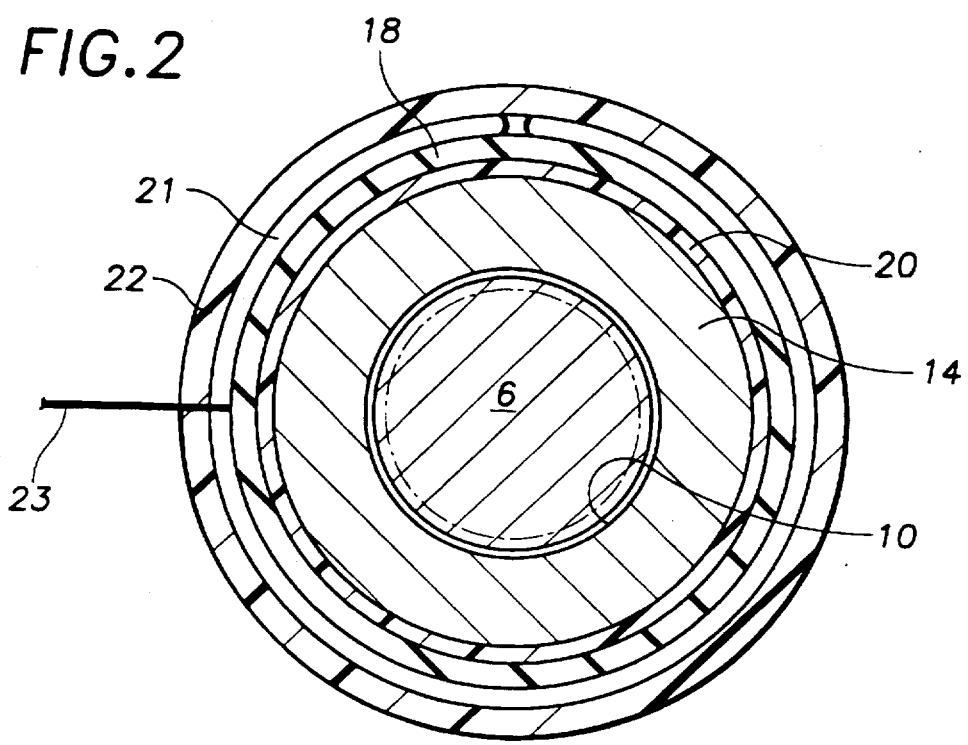
FIG. 2 is a section view on the line II—II of FIG. 1.
Figure 3:
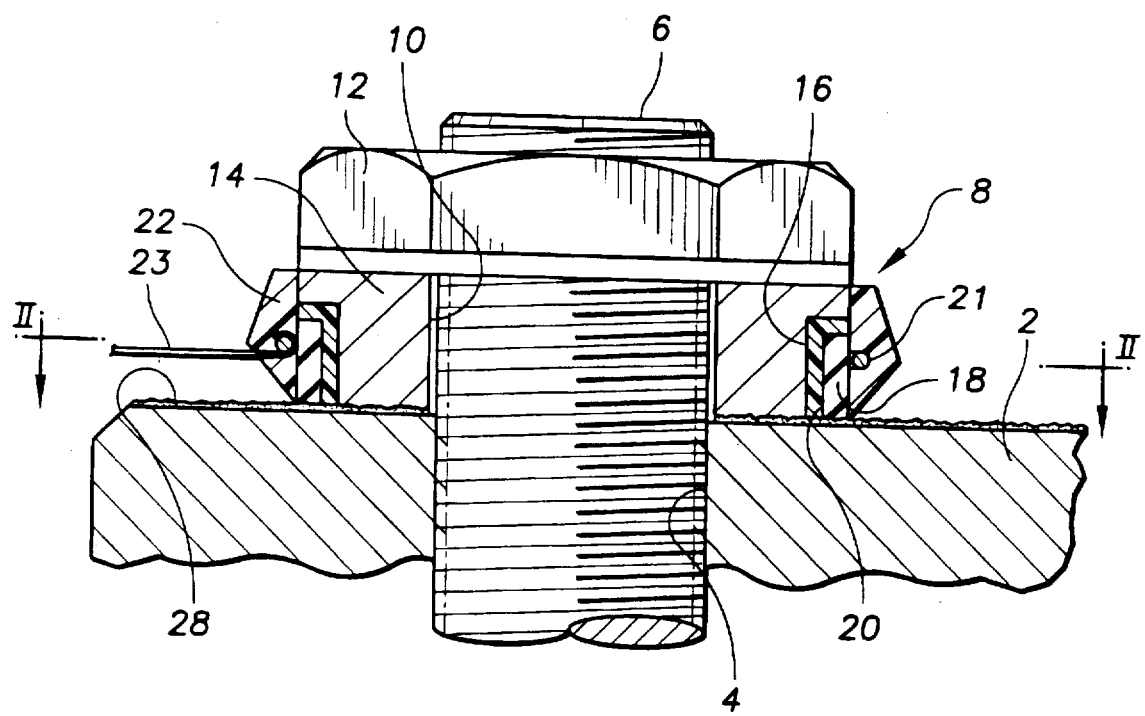
FIG. 3 is a section view similar to FIG. 1, but also showing the corrosion product.
Figure 4:
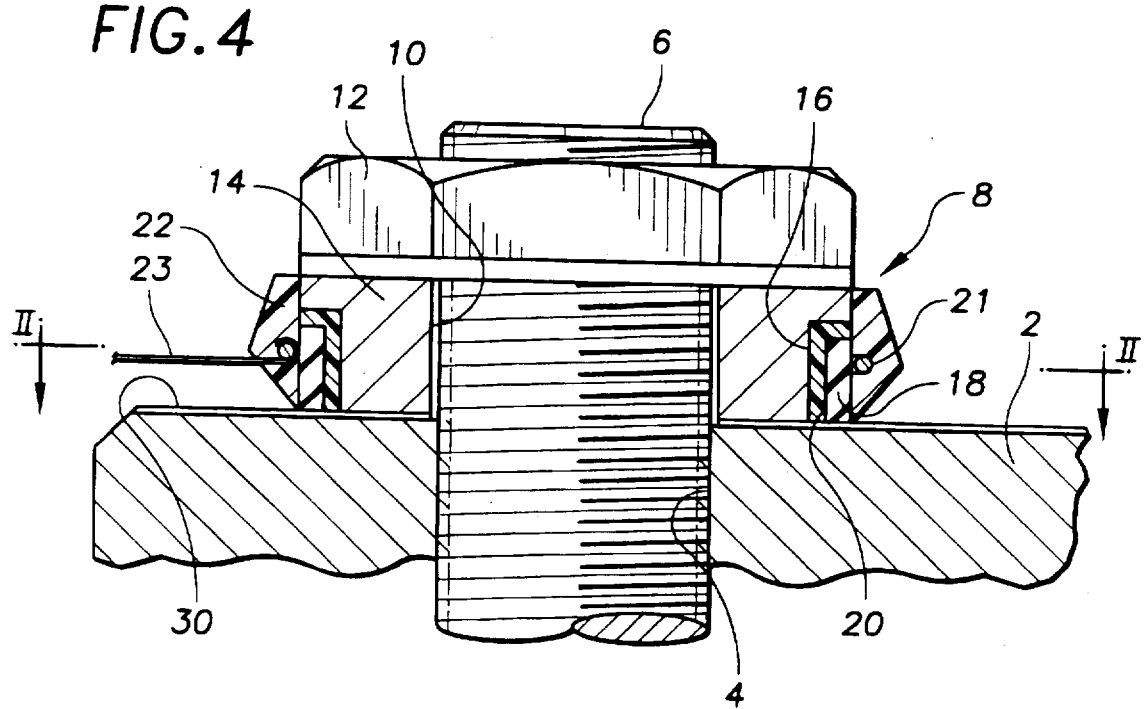
FIG. 4 is a section view similar to FIG. 1, but also showing the paint film thereon.

As seen in FIGS. 1 and 2, a body 2 of an article to be monitored, e.g. a gear box of cast magnesium alloy for use in a helicopter, is provided with a screw-threaded hole 4 into which a threaded stud 6 is screwed. A contact resistance sensor washer 8 having a bore 10 is located on the stud 6 and is held in place by a nut 12 which is screwed on to the stud.

The sensor washer 8 comprises a steel ring 14 formed with an annular recess 16 at its periphery and an electrically conducting ring 18 is located within the recess, this being confined to a narrow region at the periphery and should not impinge on the integrity of the washer to take a full mechanical load, and is separated from the steel ring by an insulating layer 20. A circling connector 21 is provided around the electrically conducting ring 18 and a resin jacket 22 extends around the periphery of the washer.

A conductor wire 23 is secured to the circling 21 and connects with a suitable resistance meter (measuring device) 40 or other data sensing and/or processing means.

The product of corrosion 28, MgO or $Mg(OH)_2$ is an electrical insulator. A resistance measurement across a contacting part 26 which is initially in good electrical contact with an un-corroded portion 24 of the magnesium alloy gear box is found to change towards a higher resistance measurement as the metallic phase at the surface interface is removed through oxidation.

In the case where the magnesium has been protected by a paint film 30 the initial contact resistance is extremely high (e.g. greater than 20 Megohm). If corrosion occurs adjacent to the washer the paint becomes cracked or holed and a conducting pathway is established. This is detected as a change in resistance from the starting value to a lower value.

In an experiment, a contact resistance sensor of the type described with reference to FIGS. 1 and 2 showed an acceptably low starting resistance as a result of the torque applied to the bolts. Further, the response appeared independent of temperature with the range −20° C. to +80° C.

Although reference has been made in the above specification to magnesium or magnesium alloy from which the gear box is made, it should be understood that the invention is not limited to a case where magnesium or magnesium alloy is necessarily the only material used.

Tests suggest that contact resistance sensors of the type described above offer simplicity in probe design and data processing Tests have shown that the sensors provide an indication of corrosion taking place or the absence of corrosion in the vicinity of the bolt fixings and also that the sensors are sensitive to the onset of corrosion and should therefore be able to indicate in advance the need for immediate maintenance.

I claim:

1. A method of detecting and monitoring corrosion, comprising the steps of:

fixing a sensor at only one position in direct contact with an uncorroded or relatively uncorroded portion of an article to be measured, making a resistance measurement between the direct contact of the sensor and the uncorroded or relatively uncorroded portion of the article to be measured, and determining corrosion based on said resistance measurement.

2. A method according to claim 1 wherein the corrosion product is an oxidation product.

3. A method according to claim 2 wherein said corrosion product is selected from the group consisting of Mgo and $Mg(OH)_2$.

4. A method according to claim 1, wherein said step of fixing provides a removable fixing of said sensor at said one position.

5. A method of detecting and monitoring corrosion, comprising the step of measuring corrosion as a change in a resistance measurement between an article to be monitored and a contact of a sensor fixed at only one position in direct contact with an initially uncorroded or relatively uncorroded portion of the article to be monitored as a result of the presence of a product of corrosion of the initially uncorroded or relatively uncorroded portion of the article.

6. A method according to claim 5 further comprising the step of detecting changes in the resistance measurement by use of a contact resistance sensor.

7. A method according to claim 6 wherein said contact resistance sensor enables measurement of changes in resistance across a contacting part, thereof initially in good contact with the uncorroded or relatively uncorroded portion of the article to be monitored.

8. A method according to claim 5 wherein the corrosion is detected as a change in a resistance value from a starting value to a higher value.

9. A method according to claim 5, wherein said sensor is removably fixed at said one position.

10. A method of detecting and monitoring corrosion, comprising the steps of:

securing a sensor at only one position in-situ to an article to be monitored, making a resistance measurement between a contact of said sensor secured at said one position and a surface of the article to be monitored, said surface having a protective coating, and determining corrosion based on said resistance measurement.

11. A method of detecting and monitoring corrosion according to claim 10 wherein said protective coating comprises paint.

12. A method according to claim 10, wherein said step of securing provides a removable securing of said sensor at said one position.

13. A method of detecting and monitoring corrosion, comprising the steps of:

securing a sensor at only one position in-situ to an article to be monitored, making a resistance measurement between a contact of said sensor secured at said one position and a surface of the article to be monitored, said surface having a protective coating, and determining damage to integrity of the protective coating as a result of corrosion in a region adjacent to the sensor by establishing a conducting pathway between the sensor and an unprotected area of the article.

14. A method of detecting and monitoring corrosion according to claim 13 wherein said corrosion is detected as a change in resistance from a starting value to a lower value.

15. A method of detecting and monitoring corrosion according to claim 13 wherein said method is capable of operating under wet or dry conditions.

16. A method according to claim 13, wherein said step of securing provides a removable securing of said sensor at said one position.

17. Apparatus for detecting and monitoring corrosion, comprising:

a contact resistance sensor for enabling measurement of changes in resistance measurement between a contact of the sensor in direct contact with an article to be monitored and an initially uncorroded or relatively uncorroded portion of said article due to the presence of a product of corrosion of the initially uncorroded or relatively uncorroded portion of the article; and a device for fixing said sensor at only one position in said direct contact with said article.

18. Apparatus according to claim 17 wherein said contact resistance sensor is located within a recess formed in a washer, and further comprising a fixing device which fixes the washer on the article to be monitored.

19. Apparatus according to claim 18 wherein said contact resistance sensor comprises a combination of electrically conductive material insulated from a body of the washer by a material and adapted to be electrically connected to means for measuring changes in resistance between the sensor and the article to be monitored.

20. Apparatus according to claim 18 wherein said recess is annular.

21. Apparatus according to claim 20 wherein said contact resistance sensor is annular so as to be received in the corresponding annular recess formed in said washer.

22. Apparatus for detecting and monitoring corrosion according to claim 17 wherein said apparatus is capable of operating under wet or dry conditions.

23. Apparatus for detecting and monitoring corrosion according to claim 17 wherein said apparatus is in combination with a resistance measuring means.

24. Apparatus according to claim 17 wherein said device includes an arrangement for removably fixing said sensor at said one position.

* * * * *